(12) United States Patent
Birk et al.

(10) Patent No.: US 7,151,270 B2
(45) Date of Patent: Dec. 19, 2006

(54) METHOD FOR CLASSIFYING OBJECT IMAGE REGIONS OF AN OBJECT TO BE DETECTED USING A SCANNING MICROSCOPE

(75) Inventors: Holger Birk, Meckesheim (DE); Rafael Storz, Heidelberg (DE)

(73) Assignee: Leica Microsystems CMS GmbH, Wetzlar (DE)

( * ) Notice: Subject to any disclaimer, the term of this patent is extended or adjusted under 35 U.S.C. 154(b) by 77 days.

(21) Appl. No.: 10/833,768

(22) Filed: Apr. 28, 2004

(65) Prior Publication Data

US 2004/0251426 A1   Dec. 16, 2004

Related U.S. Application Data

(60) Provisional application No. 60/537,768, filed on Jan. 20, 2004.

(30) Foreign Application Priority Data

May 2, 2003   (DE) ................. 103 19 946

(51) Int. Cl.
*G01N 21/64* (2006.01)
(52) U.S. Cl. ............... 250/458.1; 372/6; 372/25
(58) Field of Classification Search ............. 250/458.1; 372/6, 25
See application file for complete search history.

(56) References Cited

U.S. PATENT DOCUMENTS

| | | | |
|---|---|---|---|
| 4,779,982 A * | 10/1988 | Koshi et al. ............... 356/318 |
| 5,034,613 A | 7/1991 | Denk et al. ............... 250/458.1 |
| 5,777,732 A | 7/1998 | Hanninen et al. ........... 356/318 |
| 6,927,401 B1 * | 8/2005 | Palo ........................ 250/458.1 |
| 2003/0158470 A1 * | 8/2003 | Wolters et al. .............. 600/317 |
| 2005/0243313 A1 * | 11/2005 | Neher et al. ................ 356/317 |

FOREIGN PATENT DOCUMENTS

WO   9507447   3/1995

OTHER PUBLICATIONS

"Bio-Imaging: Multi-Spectral Imaging and Linear Unmixing Add a Whole New Dimension to Laser Scanning Fluorescence Microscopy", M.E. Dickinson et al. BioTechniques 2001, vol. 31, No. 6, 1272-1278.

\* cited by examiner

*Primary Examiner*—Renee Luebke
*Assistant Examiner*—Mary Zettl
(74) *Attorney, Agent, or Firm*—Darby & Darby

(57) ABSTRACT

A method for classifying a plurality of object image regions of an object to be detected using a scanning microscope includes labeling each of the image areas of the object with a different marker so that light of a respective characteristic emanates from each marker. The intensity of the light from each marker is detected using at least two channels so as to generate detection signals, each detection signal being a function of the intensity of the detected light. The object regions are classified using ratios of the detection signals.

25 Claims, 4 Drawing Sheets

METHOD FOR CLASSIFYING OBJECT IMAGE REGIONS OF AN OBJECT TO BE DETECTED USING A SCANNING MICROSCOPE

Priority is claimed to provisional application 60/537,768, filed Jan. 20, 2004, and to German patent application 103 19 946.2, filed May 2, 2003, the subject matters of each of which is hereby incorporated by reference herein.

The present invention relates to a method for classifying object image regions of an object to be detected using a preferably confocal scanning microscope; the object being labeled with different markers from which light of different characteristics emanates; different intensities of the light coming from the markers being detected via at least two channels; and in each case a detection signal being generated which is dependent on the detected light intensity.

BACKGROUND

Methods for classification of the type described are known. In particular, in bio-medical applications, for example, objects are labeled with very special markers of different characteristics, namely with fluorescence markers. This allows individual object regions of biological objects to be selectively labeled and represented after detection by a confocal scanning microscope. Usually, an object is labeled with several markers of different characteristics which each emit fluorescent light of a different wavelength range.

The fluorescent light of different wavelength ranges is detected by several detectors of the confocal scanning microscope which have different detection characteristics. The detectors detect the intensity of the light coming from the markers, in each case generating a detection signal which is dependent on the detected light intensity. Depending on the scanning procedure of the confocal scanning microscope, the detected detection signal is assigned to individual image elements, so-called "pixels", of a multidimensional image.

The evaluation of the detection signals or of the object images obtained therefrom is always problematic because often the wavelength ranges of the fluorescent light emitted by the markers overlap spectrally. Not least because of this, a detector detects, for example, fluorescent light that should actually be detected by another detector. This phenomenon is also referred to by the term "crosstalk". First of all, the crosstalk of an object detection can be avoided or minimized in that the wavelength ranges within which the detectors of the confocal scanning microscope detect, or are sensitive, are separated from each other to the greatest extent possible using optical filters, such as low-pass, high-pass or bandpass filters. However, this is not completely possible in cases where the wavelength ranges of the fluorescent light emitted by the markers overlap. In these cases, complete separation of the detection signals of the different detectors is not so easily possible. Furthermore, it is possible to detect only one marker during each scanning operation, for example, by illuminating the object with light of only one wavelength that is suitable for fluorescence excitation of this marker. However, when using different markers that can be excited with the same wavelength, selective excitation of the markers is then no longer possible.

Another approach is described in the literature reference "Multi-Spectral Imaging and Linear Unmixing Add a Whole New Dimension to Laser Scanning Fluorescence Microscopy", BioTechniques 2001, Vol. 31, No. 6, 1272–1278, which first gives a brief overview of the classification methods used in the prior art of which the "linear unmixing" method appears to be very particularly suitable for confocal laser scanning fluorescence microscopy. To carry out this classification method, the spectrum of the light emitted by the markers is detected for each image element or pixel by a suitable sensor. Then, the detected spectrum can be represented by a linear combination of the emission spectra of the markers. In most cases, the emission spectrum of a marker that has been used is known or can be measured so that, after the detection, the coefficients of the linear combination need to be determined, thus allowing the object regions to be classified. This can be done, for example, using methods of linear algebra. However, for this purpose, it is necessary to detect the entire emission spectrum of each object image region emitted by the marker. This is possible using the LSM 510 META confocal scanning microscope described in the literature reference, with which spectrum detection is carried out using 32 individual channels, each having a wavelength range of about 10 nm. If such a detection is not possible, the classification method presented in this literature reference produces only inadequate results.

Especially when using a number of markers of different characteristics greater than the number of available detectors of the confocal scanning microscope, detection and subsequent classification of the light coming from the individual markers is problematic because a detector capable of detecting this light more or less selectively is not available for the light of each individual marker.

SUMMARY OF THE INVENTION

It is therefore an object of the present invention to provide and further develop a method for classifying object regions of an object detected using a confocal scanning microscope, whereby a number of markers of different characteristics greater than the number of available channels or detectors can be detected and classified.

The present invention provides a method for classifying object image regions of an object to be detected using a scanning microscope. The object is labeled with different markers from which light of different characteristics emanates. Different intensities of the light coming from the markers are detected via at least two channels. In each case a detection signal is generated which is dependent on the detected light intensity. The object image regions are classified on the basis of the ratios of the detection signals.

In accordance with the present invention, it was discovered that the ratio of a detection signal of the channel of a detector or of a detector to a detection signal of a different channel of the same or a different detector is different in most cases, because generally the characteristics of the different markers differ specifically. In this respect, the object image regions can thus be classified in an advantageous manner. In this connection, crosstalk which might be present and detected by a detector is not a problem provided that the ratio of the detection signal of this channel or detector to the detection signal of a different channel or of a different detector has a value that is not obtained in any other detection signal ratioing operation. In this regard, a possible presence of crosstalk may even be desired.

An advantage of the method according to the present invention is that it allows the number of markers of different characteristic to be greater than the number of channels or detectors provided in the confocal scanning microscope.

Thus, for example, it would be possible for the light of a first marker to be detected exclusively via the channel of a first detector. The light of a second marker could be detected exclusively via a second channel of the same detector or by a different detector. Finally, the light of a third marker could be detected via a further channel of the same or a different detector; a portion of the light of the third marker that is detected via the first channel being, for example, 20 percent, and the portion of the light of the third marker that is detected via the second channel being 80 percent. Thus, by suitably selecting the characteristics of the different markers and the detection characteristics of the different channels or detectors of the confocal scanning microscope, it is possible to detect, even simultaneously, a number of different markers greater than the number of available channels or detectors—in this example, three different markers and two channels or detectors. A confocal scanning microscope that is suitable for carrying out the method according to the present invention therefore has the advantage that it does not need to have as many channels or detectors as there are different markers to be detected, and that it can therefore be produced at a lower cost while offering nearly the same functionality.

As already mentioned at the outset, the characteristic of a marker could be its fluorescent light emission, which is the case in the majority of bio-medical applications. In particular, a multiphoton fluorescence excitation is proposed, as is known, for example, in the case of two-photon fluorescence excitation, from U.S. Pat. No. 5,034,613 and German Patent DE 44 14 940, each of which is hereby incorporated by reference herein. However, the characteristic of a marker could also be its phosphorescent or chemiluminescent light emission. The capacity of the marker to change the polarization of the illuminating light could also be included here.

The "detection characteristic" of a detector is understood to be, in particular, the wavelength range in which it detects the light coming from the markers. To this end, a suitable filter that allows only light of a certain wavelength range to pass through could be arranged upstream of the detector. In this regard, a classical confocal scanning microscope system can be used for carrying out the method according to the present invention.

The spectral range in which the detector detects is in an embodiment adjusted, which could be accomplished by selectively arranging a plurality of filters having different transmission characteristics upstream of a detector. These filters could be mounted in a filter wheel.

In an embodiment, the spectral range of the detector is adjustable in a nearly infinitely variable manner. This is possible using a so-called "multiband detector", as is known, for example, from German Patent Applications DE 43 30 347 A1 and DE 199 02 625 A1, each of which is hereby incorporated by reference herein. Thus, the wavelength ranges of the individual detectors can be infinitely variably adjusted in such a manner that the detectors detect the fluorescent light emitted from different markers, and that the ratioing of the respective detection signals in each case yields a different value.

The spectral range of the detector could be adjusted automatically, in which case it would be possible to first perform a kind of a calibration measurement. After adjustment of the wavelength ranges that are detectable by the respective detectors, the fluorescent light emitted by the markers could be detected during the calibration measurement in order for the marker types present to be initially determined from the detection signals in an approximate way in an evaluation step. The spectral ranges in which the detectors detect can be automatically adjusted, especially taking into account marker characteristics that are already known. In this connection, the lower and upper wavelengths of a wavelength range of an individual detector can be taken, for example, from a database. The lower and upper wavelengths of the wavelength ranges of the detectors are preferably selected such that the ratioing of the respective detection signals in each case yields a different value.

Specifically, an object image region contains at least one image element of a scanned object image. The image element could be a pixel, which can be used as the smallest image unit of a detected image.

According to the present invention, the object image regions are classified on the basis of a ratio of a detection signal of one channel or detector to detection signals of a plurality of other channels or detectors. Thus, for example, it is possible to image six different ratios with four channels or detectors of a confocal scanning microscope; the total number of obtainable ratios being given by the number of combinations, without repetition, of the detection signal of each signal or detector with all other detection signals of the other channels or detectors. In this manner, it is advantageously possible to detect and classify—just as an example—six different markers simultaneously in one scanning operation although in this example the confocal scanning microscope has only four channels or detectors. Thus, an advantage is that a confocal scanning microscope equipped with four channels or detectors does not need to be expanded or upgraded by adding two additional channels or detectors to be able to detect six different markers simultaneously. Upgrading a confocal scanning microscope may involve very considerable outlay.

The detection of an arbitrary number of different markers is limited by noise or colocalization. Presently, it is hardly predictable at which number of markers to be detected the limit of possibility is reached.

In particular, when using fluorescent dyes as markers, the detection signals often have a relatively high noise content. Therefore, in an embodiment the noise content of the detection signals is reduced or eliminated in a process step preliminary to the classification of the object image regions. This can be accomplished, for example, by repeated detection of the same object, followed by averaging of the detection signals. It is also conceivable to filter the noise using methods of digital image processing.

Specifically, a zero point correction of the detection signals is carried out as a preliminary step to classification. This means that the absolute value corresponding to the minimum of a detection signal curve is subtracted from the detection signal curve. If the minimum of the detection signal curve has the value 0, there is no need for a zero point correction. The zero point correction ensures that the obtained detection signal ratios independently depend on the absolute shape of the detections signals.

In an embodiment, the object image regions are classified automatically. This allows fast and reproducible classification of the object image regions. Moreover, the object image regions classified in this manner are independent of the subjective perception of a microscope operator who perhaps performs a classification interactively.

In an embodiment, the object image regions are classified on the basis of a centroid of a point cloud of frequencies of occurrence of ratios obtained on a pixel-by-pixel basis. A "point cloud" is understood to be the mathematical structure that results when the frequency of occurrence of obtained ratios of two detection signals is plotted on a pixel-by-pixel basis. In this connection, in the case of noisy detection signals, there is a statistical spread, resulting in a deviation of a clearly expected ratio.

In particular, under this assumption, it is expedient to classify the object image regions allowing for an extension of the point cloud; the extension of the point cloud defining a tolerance range for the classification. In an embodiment, a ratio value that is suitable for classification is determined by searching for local frequency maxima.

The classification of the object image regions could be carried out taking into account known reference data. "Known reference data" is understood to mean, in particular, fluorescence emission spectra of the markers of different characteristics. This additional classification aid can always be used when the biologist or physician knows the markers or fluorescent dyes he/she has used to mark his/her objects, which is usually the case.

Alternatively, or in addition to the automatic classification, in an embodiment the object image regions are classified interactively. In doing so, the operator of the confocal scanning microscope sets the ratio using an input device, such as a computer mouse. Immediately after setting the ratio, the result image or result classification is displayed to the operator on an output device, such as a computer monitor. This operation is repeated until the classification produces a satisfactory result for the operator.

In order to classify the object image regions, in an embodiment a multidimensional representation is generated. In the representation, frequencies of occurrence of the ratios of the detection signals are plotted against each other on a pixel-by-pixel basis. Ideally, this results in ratio values lying on a straight line unless the detection signals are noisy. Since, especially in fluorescence microscopy, the detection signals are noisy, in this case, a point cloud is obtained which is essentially distributed about a straight line in a scattered manner.

The ratio between a detection signal of one detector and the detection signal of a different detector is defined by the gradient of a straight line which can be positioned in the multidimensional representation. For the purpose of interactive classification, the operator positions a straight line in the multidimensional representation. Depending on the control software, the straight line can be positioned, for example, using a computer mouse. In order to check the classification result, a result image could be output to the operator each time a straight line has been positioned.

For successful classification in cases where the ratio values plotted in the multidimensional representation scatter about a straight line in the form of a point cloud, in an embodiment a defined ratio is assigned a tolerance range to which the same classification applies. In this connection, the defined ratio may have been determined or found by either automatic or interactive classification. In this regard, even object image regions whose ratio values would normally not be considered in the classification for an object part are nevertheless classified as belonging to this object part and assigned thereto, taking into account a possibly existing noise content of the detection signals.

To visually support the interactive classification, in an embodiment a projection onto a color polygon is carried out. This means the following: as indicated in the case of the linear unmixing method, different fluorescence markers can altogether produce a fluorescent light emission which emanates from the markers and which can be represented in the form of a linear combination of the individual emission spectra of the markers.

In order to further refine the classification, in an embodiment the object image regions are classified in conjunction with the linear unmixing method. Ultimately, the linear unmixing method mentioned at the outset can support the classification method of the present invention in order to further refine the classification results. In the case that the number of markers of different characteristics is greater than the number of available detectors, the linear system of equations of the linear unmixing method would initially be underdetermined. Therefore, for example, artificial additional detectors or detection signals could be generated to arrive at a solvable linear equation system. The artificial additional detection signals can be generated by ratioing between two detection signals of two detectors. Alternatively, in an embodiment the components of the total of detected detection signals that can be clearly classified without ratioing are first classified. Then, the linear unmixing method may be used to classify the remaining object image regions.

In principle, the light emitted by the markers may be detected sequentially. However, this may be time-consuming, especially when several different markers are present, and, in addition, can lead to bleaching of the fluorescent marker dyes. Therefore, in an embodiment the light coming from the markers is detected simultaneously. In this manner, the total recording time of the object is advantageously reduced.

BRIEF DESCRIPTION OF THE DRAWINGS

The present invention is elaborated upon below based on an embodiment with reference to the drawings.

DETAILED DESCRIPTION

Figure 1:
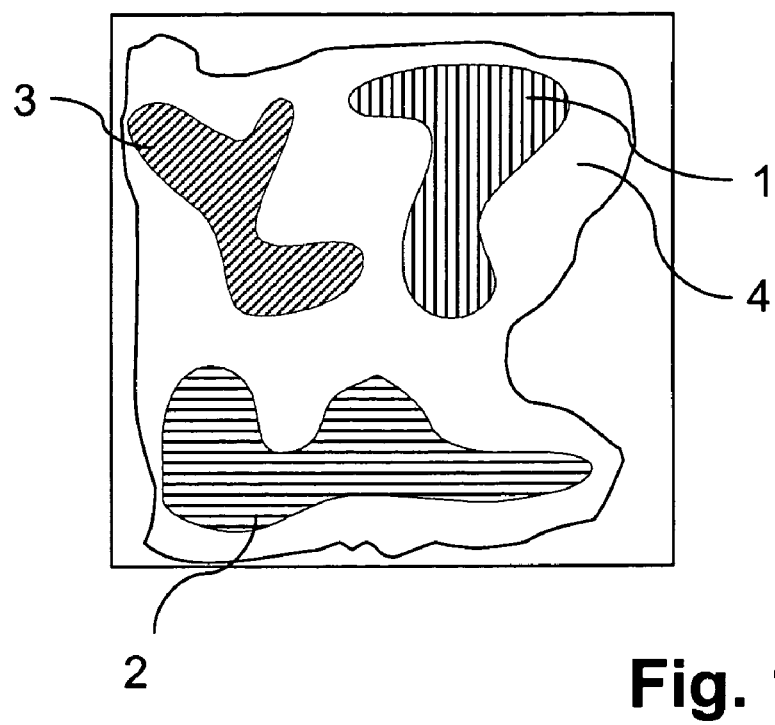
FIG. 1 is a schematic representation of several object regions of an object which was detected using a confocal scanning microscope.

A method for classifying object image regions 1, 2, 3 of an object 4 detected using a confocal scanning microscope will be explained with reference to FIGS. 1 through 6*c*. Object 4 is labeled in some regions with three markers of different characteristics. Light of different characteristics emanates from the markers; this light being fluorescent light. The emission spectra of the three different markers are shown in the diagram of FIG. 2; the spectrum of the marker of object image region 1 being denoted by reference numeral 5, the spectrum of the marker of object image region 2 by reference numeral 6, and the spectrum of the marker of object image region 3 being referred to by reference numeral 7.

Figure 2:
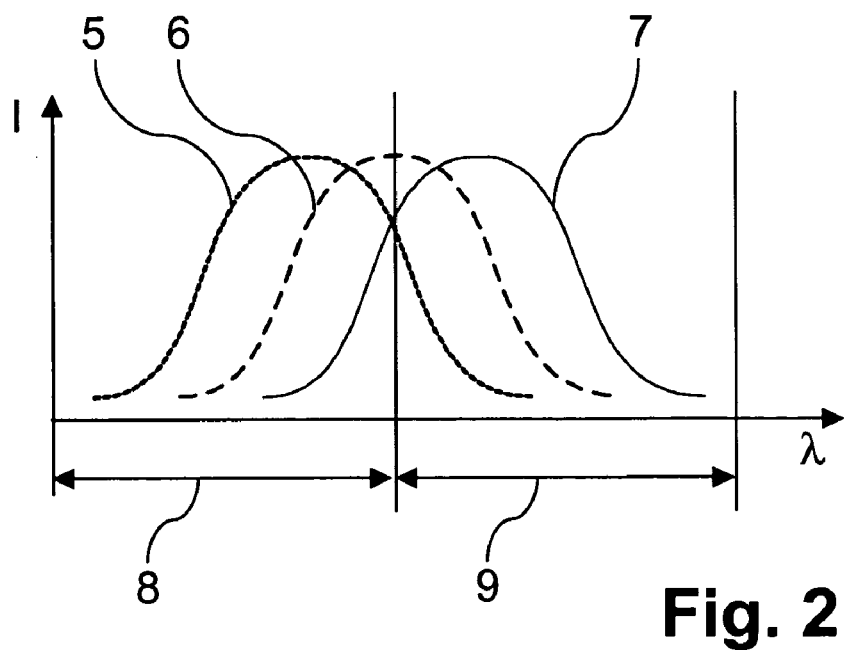
FIG. 2 is a schematic diagram showing the emission spectra of the used fluorescent dyes with which the object regions of FIG. 1 are labeled.

A confocal scanning microscope contains, for example, one detector having two channels of different detection characteristics, or two detectors of different detection characteristics; the one channel or detector detecting the intensity of the light coming from the markers in a wavelength range which is indicated by double arrow 8 in FIG. 2. Analogously, the second channel or detector detects the intensity of the light coming from the markers in the wavelength range which is indicated by double arrow 9. The two channels or detectors each generate a detection signal which is dependent on the detected light intensity. The number of markers of different characteristics is greater than the number of channels or detectors, respectively. There are provided three different markers and two different channels or detectors, respectively. The light of at least one marker, especially of the marker that marks object region 2, is detected by the two channels or detectors proportionally according to the wavelengths of the channels or detectors.

According to the present invention, the object image regions 1, 2, 3 are classified on the basis of the ratios of the detection signals.

Figure 3:
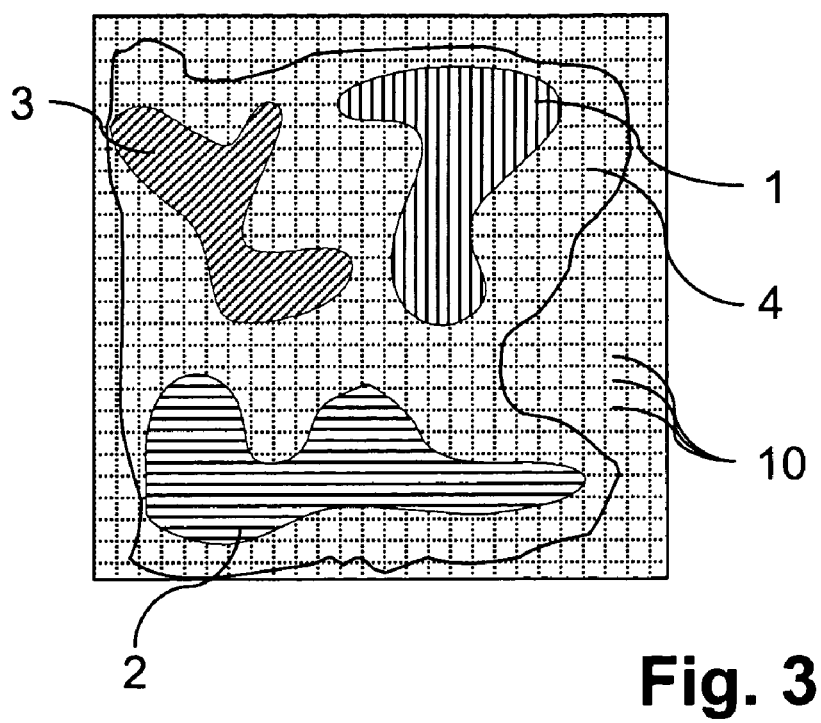
FIGS. 3 and 4 each are schematic views of an image which, in each case, was detected by a respective detector of the confocal scanning microscope.
Figure 4:
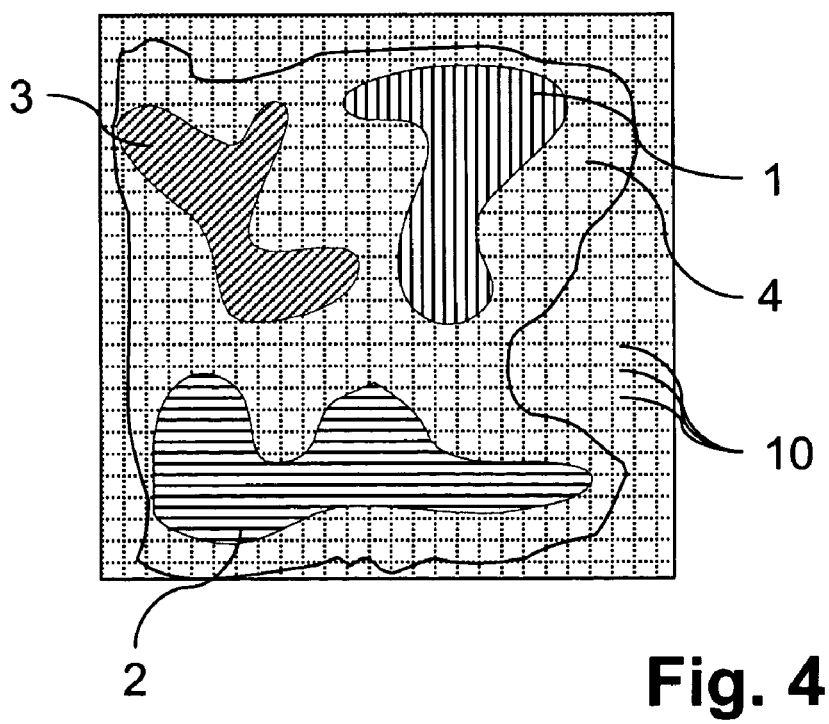

The object image regions 1, 2, 3 shown in FIGS. 3 and 4 each contain a plurality of image elements; the image elements being individual pixels 10. For better illustration, pixels 10 are shown larger than actual size. The image shown in FIG. 3 was detected via the first channel of the first detector or by the first detector of the confocal scanning microscope. The image shown in FIG. 4 was detected by the second channel of the detector or by the second detector of the confocal scanning microscope. The images shown in FIGS. 3 and 4 exhibits different intensity values or gray-scale values which, however, are not shown in the schematic representation.

Figure 5:
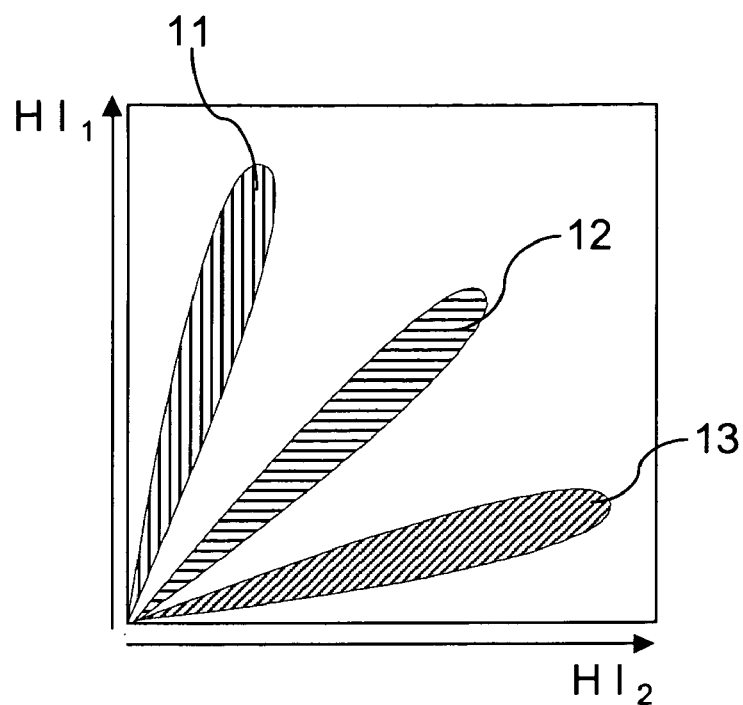
FIG. 5 is a schematic diagram in which the frequencies of occurrence of the ratios of the detection signals of the two detectors are plotted against each other on a pixel-by-pixel basis.

Object image regions 1, 2, 3 are classified interactively. In order to classify object image regions 1, 2, 3, a two-dimensional representation is generated in the form of a diagram, which is shown in FIG. 5. In this diagram, the pixel-by-pixel frequencies of occurrence 11, 12, 13 of the ratios of the detection signals are plotted against each other. The pixel-by-pixel frequencies of occurrence $HI_2$ of the ratio values of the detection signals detected via the second channel or by the second detector are plotted on the abscissa, while the pixel-by-pixel frequencies of occurrence $HI_1$ of the ratio values detected via the first channel or by the first detector are plotted on the ordinate. In this context, the frequencies of occurrence 11 of the ratio values of the detection signals of the two channels or detectors correspond to the emission spectrum of the marker with which object image region 1 is labeled. Analogously, the frequencies of occurrence 12 and 13 denote the ratio values of the detection signals of the two channels or detectors that correspond to the emission spectra of the markers with which object image regions 2 and 3 are labeled, respectively.

Figure 6A:
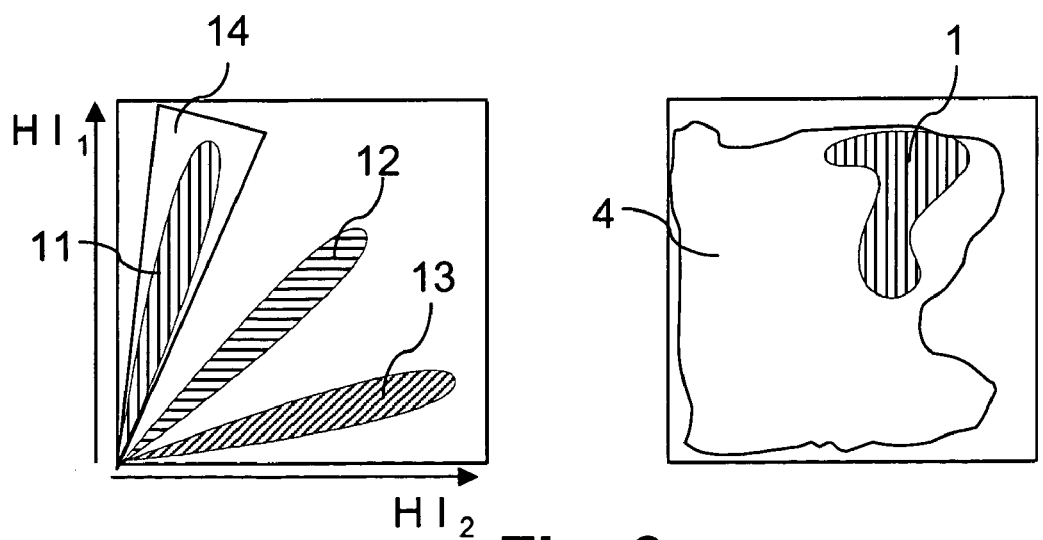
FIGS. 6*a* through *c* each show, on the left side, a schematic representation of a diagram according to FIG. 5, which, in each case, shows a tolerance range for the pixel-by-pixel frequencies of occurrence of the ratios; while on the right side, a classified object image region is shown, respectively.
Figure 6B:
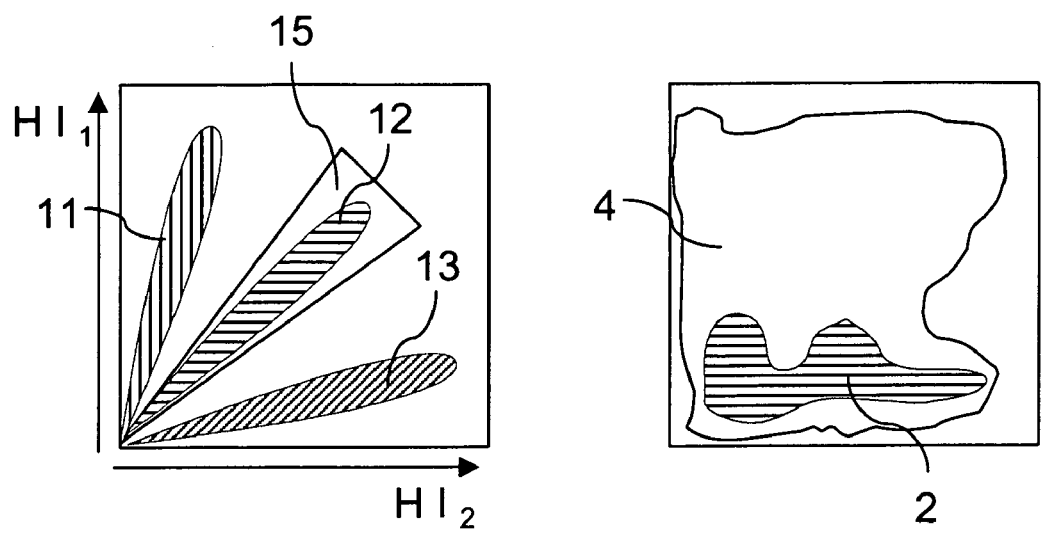

Each defined ratio 11, 12, 13 is assigned a tolerance range 14, 15, 16 to which the same classification applies. This is schematically shown in the diagrams on the left side of FIGS. 6a through 6c. All pixels 10 or image regions of an object image whose ratio values lie within tolerance range 14 are classified as belonging to object image region 1, which is indicated in the right diagram in FIG. 6a. Analogously, object image region 2 in the right diagram of FIG. 6b is classified by the ratio values lying in tolerance range 15.

Figure 6C:
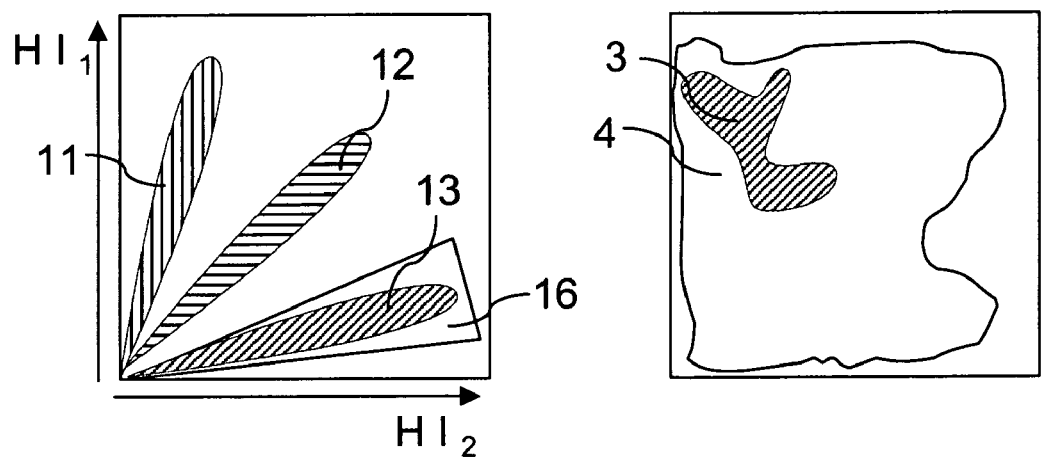

Finally, object image region 3 in the right diagram of FIG. 6c is classified by the ratio values lying in tolerance range 16.

To conclude, it should be pointed out very particularly that the exemplary embodiments discussed above serve only to illustrate the claimed teaching without limiting it to the exemplary embodiments.

What is claimed is:

1. A method for classifying a plurality of object image regions of an object to be detected using a scanning microscope, comprising:
   labeling each of the image areas of the object with a different respective marker so that respective light of a respective characteristic emanates from each respective marker;
   detecting a respective intensity of the respective light from each respective marker using at least two channels so as to generate respective detection signals, each respective detection signal being a function of the respective intensity of the respective detected light; and
   classifying the object regions using ratios of the respective detection signals;
   wherein the classifying is performed automatically, and wherein the classifying is performed using a centroid of a point cloud of frequencies of occurrence of the ratios on a pixel-by-pixel basis.

2. The method as recited in claim 1 wherein the scanning microscope is a confocal scanning microscope.

3. The method as recited in claim 1 wherein the at least two channels include a first and a second channel of a first detector.

4. The method as recited in claim 1 wherein the at least two channels include a first channel of a first detector and a second channel of a second detector.

5. The method as recited in claim 1 wherein the respective light of a respective characteristic of each marker is a respective fluorescent light emission of the respective marker.

6. The method as recited in claim 1 wherein the at least two channels are included in at least one detector, the at least one detector having a detection characteristic, the detection characteristic being a spectral range of detection of the at least one detector.

7. The method as recited in claim 1 wherein the at least two channels are included in at least one detector having at least one adjustable spectral range.

8. The method as recited in claim 7 wherein at least one adjustable spectral range is adjustable in a nearly infinitely variable manner.

9. The method as recited in claim 7 further comprising adjusting the at least one adjustable spectral range automatically.

10. The method as recited in claim 9 wherein the adjusting is performed based on a known marker characteristic.

11. The method as recited in claim 1 wherein at least one of the object image regions includes at least one image element.

12. The method as recited in claim 1 wherein:
    the at least two channels include three channels; and
    the classifying is performed based on a respective ratio of a first detection signal of a first channel of the three channels to respective second and third detection signals of a second and third channel of the three channels.

13. The method as recited in claim 1 wherein:
    the at least two channels include a first channel of a first detector, a second channel of a second detector and a third channel of a third detector; and the classifying is performed based on a respective ratio of a respective detection signal of the first channel to respective detection signals of the second and third channels.

14. The method as recited in claim 1 further comprising reducing or eliminating a noise content of the detection signals.

15. The method as recited in claim 1 further comprising performing a zero point correction of the detection signals.

16. The method as recited in claim 1 wherein the classifying is performed allowing for an extension of the point cloud, the extension of the point cloud defining a tolerance range for the classifying.

17. The method as recited in claim 1, wherein the classifying is performed based on known reference data.

18. The method as recited in claim 1 wherein the classifying is performed interactively.

19. The method as recited in claim 18 further comprising performing a projection onto a color polygon.

20. The method as recited in claim 1 wherein the classifying is performed using a linear unmixing method.

21. The method as recited in claim 1 wherein the detecting is performed so as to simultaneously detect the respective intensity of the respective light from the respective markers.

22. A method for classifying a plurality of object image regions of an object to be detected using a scanning microscope, comprising:
  labeling each of the image areas of the object with a different respective marker so that respective light of a respective characteristic emanates from each respective marker;
  detecting a respective intensity of the respective light from each respective marker using at least two channels so as to generate respective detection signals, each respective detection signal being a function of the respective intensity of the respective detected light; and
  classifying the object regions using ratios of the respective detection signals;
wherein the classifying is performed interactively, and wherein the classifying is performed using a plotting of frequencies of occurrence of the ratios against each other on a pixel-by-pixel basis so as to generate a multidimensional representation.

23. The method as recited in claim 22 wherein the ratios include a first ratio between a first detection signal of a first channel of the at least two channels and a second detection signal of a second channel of the at least two channels, and further comprising defining the first ratio by a gradient of a straight line positionable in the multidimensional representation.

24. The method as recited in claim 23 wherein the first channel is respective channel of a first detector and the second channel is a respective channel of a second detector.

25. The method as recited in claim 22 further comprising assigning to the first ratio a tolerance range, a same classification applying to the tolerance range.

* * * * *